(12) United States Patent
Grey et al.

(10) Patent No.: US 6,194,591 B1
(45) Date of Patent: Feb. 27, 2001

(54) AQUEOUS EPOXIDATION PROCESS USING MODIFIED TITANIUM ZEOLITE

(75) Inventors: Roger A. Grey; Rangasamy Pitchai, both of West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/559,287

(22) Filed: Apr. 27, 2000

(51) Int. Cl.$^7$ ............................ C01D 301/12; B01J 21/16
(52) U.S. Cl. ..................... 549/533; 502/66; 502/262; 549/531; 549/523
(58) Field of Search .................... 549/533, 531, 549/523; 502/66, 262

(56) References Cited

U.S. PATENT DOCUMENTS

| | | | |
|---|---|---|---|
| 3,351,635 | 11/1967 | Kollar | 260/348.5 |
| 4,367,342 | 1/1983 | Wulff et al. | 549/529 |
| 4,410,501 | 10/1983 | Taramasso et al. | 423/326 |
| 4,833,260 | 5/1989 | Neri et al. | 549/531 |
| 5,859,265 | 1/1999 | Müller et al. | 549/531 |
| 6,008,389 | * 12/1999 | Grosch et al. | 549/533 |
| 6,063,942 | * 5/2000 | Grey | 549/523 |

FOREIGN PATENT DOCUMENTS

| | | |
|---|---|---|
| 1001038A7 | 6/1989 | (BE) . |
| 4-352771 | 12/1992 | (JP) . |
| WO 98/00413 | 1/1998 | (WO) . |

OTHER PUBLICATIONS

*Journal of Catalysis* 129, 159–167 (1991).

* cited by examiner

*Primary Examiner*—Charanjit S. Aulakh
(74) *Attorney, Agent, or Firm*—Kevin M. Carroll

(57) ABSTRACT

An olefin epoxidation process is described. The process comprises epoxidizing an olefin with hydrogen peroxide in the presence of a modified titanium zeolite catalyst in water solvent. The titanium zeolite catalyst is modified with a platinum, palladium or copper compound. The modified catalyst unexpectedly increases olefin epoxidation activity.

20 Claims, No Drawings

AQUEOUS EPOXIDATION PROCESS USING MODIFIED TITANIUM ZEOLITE

FIELD OF THE INVENTION

This invention relates to an epoxidation process using a modified titanium zeolite catalyst and hydrogen peroxide in water solvent. Surprisingly, the modified catalyst shows improved activity in aqueous olefin epoxidation compared to the unmodified catalyst.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst.

Much current research is conducted in the direct epoxidation of olefins with oxygen and hydrogen. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

Besides oxygen and alkyl hydroperoxides, another oxidizing agent useful for the preparation of epoxides is hydrogen peroxide. U.S. Pat. No. 4,833,260, for example, discloses olefin epoxidation using hydrogen peroxide and a titanium silicate zeolite. The preferred solvent for this reaction is water due to the cost and availability of aqueous hydrogen peroxide. However, the reaction in water proceeds at low rates and a co-solvent is necessary to give sufficient productivity to epoxide. Clerici, et al., *J. Catal.* (1991) 129, 159, for example, teach that a water concentration above 50 weight percent considerably decreases the rate of reaction in propylene epoxidation. The Clerici article also teaches that methanol is considered the best solvent for the epoxidation of propylene. Thus, one distinct disadvantage of olefin epoxidation with hydrogen peroxide by titanium zeolites is the need for expensive co-solvents. This requirement results in additional expense for olefin epoxidation processes using hydrogen peroxide.

In sum, new processes that would allow the aqueous epoxidation of olefins using hydrogen peroxide are needed. Particularly valuable processes would result in increased productivity to epoxide.

SUMMARY OF THE INVENTION

The invention is an olefin epoxidation process that comprises reacting an olefin with hydrogen peroxide in water solvent in the presence of a modified titanium zeolite catalyst. The modified catalyst comprises a titanium zeolite chemically treated with the addition of palladium, platinum, or copper compounds. We surprisingly found that the modified catalysts give significantly higher activity in the aqueous epoxidation of olefins compared to unmodified catalysts.

DETAILED DESCRIPTION OF THE INVENTION

The process of the invention employs a catalyst that comprises a titanium zeolite chemically treated with a platinum, palladium, or copper modifier. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The titanium zeolite catalyst is chemically modified by treatment with a palladium, platinum, or copper compound, or mixtures thereof. We surprisingly found that modification of the titanium zeolite is crucial for improving the activity of titanium zeolite catalysts in olefin epoxidation reactions with hydrogen peroxide in water.

There are no particular restrictions regarding the choice of palladium, platinum or copper compounds used as the modifier. For example, suitable compounds include the nitrates, sulfates, halides (e.g., chlorides, bromides), carboxylates (e.g., acetate), and amine complexes of palladium; the halides, acetylacetonates, and amine complexes of platinum; and the nitrates, sulfates, halides, hydroxides, carboxylates, acetylacetonates, and amine complexes of copper. Also, cationic copper and palladium compounds stabilized with an anion such as $BF_4^-$ or $PF_6^-$ are useful as modifiers. Particularly preferred modifiers include $CuCl_2$, $PdBr_2$, $PdCl_2$, $Pt(NH_3)_4Cl_2$, $Pd(NH_3)_4Br_2$, $Pd(NH_3)_4Cl_2$, Pd(NH$_3$)$_4$(NO$_3$)$_2$, (CH$_3$CN)$_2$PdCl$_2$, and (CH$_3$CN)$_2$Pd(BF$_4$)$_2$. If palladium halides such as PdBr$_2$ or PdCl$_2$ are used, NH$_4$OH is typically added to solubilize the compounds before impregnation or exchange.

The modifier is added to the titanium zeolite in an amount preferably in the range of about from about 0.01 to 10 weight percent of Pd, Pt, or Cu, more preferably from about 0.01 to 5 weight percent of the modifier metal (Pd, Pt, or Cu), and most preferably from about 0.01 to 2 weight percent of the modifier metal. The manner in which the modifier is incorporated into the catalyst is not considered to be particularly critical. For example, the modifier can be incorporated into the zeolite by ion-exchange. Alternatively, the modifier may be supported on the zeolite by impregnation or the like.

After modifier incorporation, the catalyst may be recovered prior to use in olefin epoxidation or may be used directly in olefin epoxidation without recovering a solid catalyst. Suitable catalyst recovery methods include filtration and washing, rotary evaporation and the like. The catalyst is typically dried at a temperature greater than 40° C. prior to use in epoxidation. The catalyst may additionally comprise a binder or the like and may be molded, spray dried, shaped or extruded into any desired form prior to use in epoxidation. If the catalyst is not recovered prior to use in olefin epoxidation, some of the palladium, platinum or copper modifier may still be soluble in solution during epoxidation.

The oxidation state of the Pd, Pt, or Cu is not considered critical. The modifier metal may be in an oxidation state anywhere from 0 to +4 or any combination of such oxidation states. The modifier metal may be fully or partially reduced after addition to the titanium zeolite. However, it is preferable not to reduce the Pd, Pt, or Cu after addition to the titanium zeolite, but leave the metal in its oxidized state.

The epoxidation process of the invention comprises contacting an olefin and hydrogen peroxide in the presence of the modified titanium zeolite catalyst in water solvent. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing C$_2$–C$_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide is generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting metal-catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0–150° C., more preferably, 20–120° C. Reaction or residence times of from about 1 minute to 48 hours, more preferably 1 minute to 8 hours will typically be appropriate. It is advantageous to work at a pressure of 1 to 100 atmospheres, although the reaction can also be performed at atmospheric pressure.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

The following examples merely illustrate the invention. Those skilled in the art will recognize many variations that are within the spirit of the invention and scope of the claims.

EXAMPLE 1

PREPARATION OF Pt/TS-1 BY ION EXCHANGE

TS-1 can be made according to any known literature procedure. See, for example, U.S. Pat. No. 4,410,501, DiRenzo, et. al., *Microporous Materials* (1997), Vol. 10,283, or Edler, et. al., *J. Chem. Soc., Chem. Comm.* (1995), 155. The TS-1 is calcined at 550° C. in air for 4 hours before use.

Pt(NH$_3$)$_4$Cl$_2$ (1 g) is added to 130 grams of deionized water in a 250-mL beaker equipped with a magnetic stir bar, followed by 30% aqueous ammonium hydroxide (13 g). Titanium silicalite (TS-1, 26 g, 2.1 wt. % titanium) is added over a 5 minute period to this solution, then the slurry is stirred at 23° C. for 24 hrs. The water is removed by decantation after centrifuging the slurry. The catalyst is washed with deionized water (4×100 mL) by slurrying the catalyst in water, centrifuging, and decanting the water. The catalyst is dried in a vacuum oven (1 torr) at 50° C. for 6 hrs. The catalyst (Catalyst 1) analyzed for 2.2 wt. % platinum, 2.1 wt. % titanium, 0.66 wt. % nitrogen and less than 0.01 wt. % chloride.

Catalyst 1A was prepared by the above procedure but with only 0.5 g of Pt(NH$_3$)$_4$Cl$_2$.

EXAMPLE 2

PREPARATION OF Pd/TS-1 BY ION EXCHANGE

Pd(NH$_3$)$_4$Cl$_2$ (0.37 g) is added to 300 grams of deionized water in a 1-L beaker equipped with a magnetic stir bar, followed by 30% aqueous ammonium hydroxide (30 g). Titanium silicalite (TS-1, 30 g, 2.1 wt. % titanium) is added over a 5 minute period to this solution, then the slurry is stirred at 23° C. for 24 hrs. The water is removed by decantation after centrifuging the slurry. The catalyst is washed with deionized water (5×100 mL) by slurrying the catalyst in water, centrifuging, and decanting the water. The catalyst is dried in a vacuum oven (1 torr) at 55° C. for 3 hrs.

The catalyst (Catalyst 2) analyzed for 0.4 wt. % palladium, 2.1 wt. % titanium, 0.77 wt. % nitrogen and less than 0.01 wt. % chloride.

EXAMPLE 3

PREPARATION OF Pd/TS-1 BY IMPREGNATION

Palladium dibromide (0.377 g) is dissolved in 30% aqueous ammonium hydroxide (50 g) in a 250-mL flask equipped with a magnetic stir bar. Deionized water (60 g) is added to the solution, followed by addition of TS-1 (30 g, 2.12 wt. % titanium) over a 5 minute period. The slurry is stirred at 23° C. for 0.5 hr, then the solvent is removed by rotoevaporation at 55° C. The solids are dried in a vacuum oven (1 torr) at 50° C. for 4 hrs. The catalyst (Catalyst 3) analyzed for 0.5 wt % palladium, 2.1 wt % titanium, 0.7 wt % bromine and 0.37 wt % nitrogen.

EXAMPLE 4

PREPARATION OF Cu/TS-1 (IN-SITU PREPARATION)

In an Erlenmeyer flask, a stock solution containing copper dichloride (60 mg) in deionized water (30 g) and 30% aqueous ammonium hydroxide (120 mg) is prepared. The stock solution (3 g) is added to TS-1 (250 mg, 2.1 wt. % titanium) in deionized water (31 g), and the resulting mixture is stirred for 10 minutes. Hydrogen peroxide (8 g, 30 wt. % aqueous) is added to the catalyst slurry. The mixture is used in Example K.

EXAMPLE 5

PREPARATION OF Pt/TS-1 (IN-SITU PREPARATION)

A stock solution of $(NH_3)_4PtCl_2.H_2O$ (80 mg) in deionized water (200 g) is prepared in an Erlenmeyer flask. The stock solution (22 g) is added to a reactor containing TS-1 (0.25 g, 2.1 wt. % titanium) and the mixture is stirred for 24 hrs. An additional 10 g of water, followed by hydrogen peroxide (8 g, 30 wt. % aqueous), is added to the catalyst slurry. The mixture is used in Example L.

COMPARATIVE EXAMPLE A

PROPYLENE EPOXIDATION WITH HYDROGEN PEROXIDE USING TS-1 IN METHANOL SOLVENT

A 100-mL pressure reactor equipped with a magnetic stir bar is charged with methanol (34 g). TS-1 (250 mg, 2.1 wt. % titanium) is then added, followed by hydrogen peroxide (8 g, 30 wt. % aqueous, 71 mmol of $H_2O_2$). The reaction mixture is pressurized with nitrogen to 400 psig and vented three times. Propylene (14 g, 333 mmol) is transferred from a 50-mL pressure Hoke vessel with 400 psig of nitrogen. The pressure of the reactor is then raised to 400 psig with nitrogen and the vessel is sealed. The reaction mixture is heated and maintained at the reaction temperature (see Table 1) for 30 minutes before cooling to 23° C.

Both the gas and liquid phase samples are collected and analyzed by gas chromatography (GC). First, the gases are vented into a gas bag for GC analysis. Then, the reactor is pressurized to 400 psig with nitrogen and the gases vented into a second gas bag for GC analysis. The liquid (40.8 g) is then recovered from the reactor and analyzed by GC for organic products and iodiometric titration for hydrogen peroxide. The results and the reaction temperature are shown in Table 1. In this run, 6.9 mmol of methoxyethers also formed as byproducts.

COMPARATIVE EXAMPLES B–C

EPOXIDATION OF PROPYLENE WITH HYDROGEN PEROXIDE USING TS-1 IN WATER SOLVENT

The epoxidation reaction is run according to the same procedure as Comparative Example A except that water (34 g) is used as a solvent instead of methanol.

The results as shown in Table 1 demonstrate that the reaction rate of epoxidation using TS-1 in water is very low compared to the rate in methanol.

EXAMPLES D–H

EPOXIDATION OF PROPYLENE WITH HYDROGEN PEROXIDE USING CATALYST 1 IN WATER SOLVENT

The epoxidation reaction is run according to the same procedure as Comparative Example B except that the catalyst is the Pt/TS-1 catalyst produced in Example 1.

EXAMPLES I–J

EPOXIDATION OF PROPYLENE WITH HYDROGEN PEROXIDE USING CATALYST 2 IN WATER SOLVENT

The epoxidation reaction is run according to the same procedure as Comparative Example B except that the catalyst is the Pd/TS-1 catalyst produced in Example 2.

EXAMPLE K

EPOXIDATION OF PROPYLENE WITH HYDROGEN PEROXIDE USING CATALYST 3 IN WATER SOLVENT

The epoxidation reaction is run according to the same procedure as Comparative Example B except that the catalyst is the Pd/TS-1 catalyst produced in Example 3.

EXAMPLE L

EPOXIDATION OF PROPYLENE WITH HYDROGEN PEROXIDE USING CATALYST 4 IN WATER SOLVENT

The Cu/TS-1 catalyst mixture prepared in Example 4 is charged into a 100-mL pressure reactor equipped with a magnetic stir bar. The reaction mixture is pressurized with nitrogen to 400 psig and vented three times. Propylene (14 g, 333 mmol) is transferred from a 50-mL pressure Hoke vessel with 400 psig of nitrogen. The pressure of the reactor is then raised to 400 psig with nitrogen and the vessel is sealed. The reaction mixture is heated to the reaction temperature for 30 minutes before cooling to 23° C.

Both the gas and liquid phase samples are collected and analyzed by gas chromatography (GC) as in Comparative Example A.

EXAMPLE M

EPOXIDATION OF PROPYLENE WITH HYDROGEN PEROXIDE USING CATALYST 5 IN WATER SOLVENT

The epoxidation is run according to the same procedure as Example K except that the catalyst mixture is the Pt/TS-1 catalyst produced in Example 5.

The epoxidation results, in Table 1, show that the use of a modified titanium zeolite catalyst leads to an unexpected improvement in productivity for the epoxidation of propylene with hydrogen peroxide in water compared to an unmodified TS-1. Modified catalysts 1–5 in Examples D-M produce from 2 to 10 times more PO equivalents (PO+PG+ acetol) compared to unmodified TS-1 in Comparative Examples B and C.

TABLE 1

Effect of Modifier on Titanium Zeolite Catalyst Activity in the Aqueous Epoxidation of Propylene with Hydrogen Peroxide

| Example | Catalyst # | Temp (° C.) | Solvent | PO produced (mmol) | PG produced (mmol) | Acetol produced (mmol) |
| --- | --- | --- | --- | --- | --- | --- |
| A* | TS-1 | 40 | methanol | 49 | 0.53 | |
| B* | TS-1 | 40 | water | 2 | | |
| C* | TS-1 | 60 | water | 1.8 | 0.02 | |
| D | 1 (2% Pt/TS-1) | 40 | water | 6.6 | | |
| E | 1 (2% Pt/TS-1) | 60 | water | 14 | | |
| F | 1 (2% Pt/TS-1) | 60 | water | 17.8 | 0.64 | 0.55 |
| G | 1 (2% Pt/TS-1) | 80 | water | 16 | 3.2 | 0.84 |
| H | 1A (1% Pt/TS-1) | 60 | water | 10.2 | | |
| I | 2 (0.4% Pd/TS-1) | 40 | water | 9.3 | | |
| J | 2 (0.4% Pd/TS-1) | 60 | water | 10 | | |
| K | 3 (0.5% Pd/TS-1) | 60 | water | 13 | 0.16 | |
| L | 4 (1% Cu/TS-1) | 60 | water | 9.6 | 0.37 | 0.08 |
| M | 5 (2% Pt/TS-1) | 60 | water | 5.3 | 14.9 | |

*Comparative Example.

We claim:

1. A process for producing an epoxide comprising reacting an olefin with hydrogen peroxide in water solvent in the presence of a catalyst comprising a titanium zeolite wherein the titanium zeolite is chemically treated with a modifier selected from the group consisting of palladium, platinum, and copper compounds.

2. The process of claim 1 wherein the zeolite is titanium silicalite.

3. The process of claim 1 wherein the zeolite is TS-1.

4. The process of claim 1 wherein the catalyst is comprised of from 0.01 to 5 weight percent of the modifier metal.

5. The process of claim 1 wherein the catalyst is comprised of from 0.01 to 2 weight percent of the modifier metal.

6. The process of claim 1 wherein the modifier metal is in an oxidized state.

7. The process of claim 1 wherein the olefin is a $C_2$–$C_6$ olefin.

8. The process of claim 1 wherein the olefin is propylene.

9. The process of claim 1 wherein the molar ratio of hydrogen peroxide to olefin in the range of from about 10:1 to about 1:10.

10. The process of claim I wherein the process is performed at a temperature from about 20° C. to about 120° C.

11. A process for producing an epoxide comprising reacting an olefin with hydrogen peroxide in water solvent in the presence of a catalyst comprising a titanium zeolite chemically treated with a modifier selected from the group consisting of palladium, platinum, and copper compounds, wherein the modifier is added as a solution and the catalyst is recovered and dried before use prior to use in olefin epoxidation.

12. The process of claim 11 wherein the zeolite is titanium silicalite.

13. The process of claim 11 wherein the catalyst is comprised of from 0.01 to 2 weight percent of the modifier metal.

14. The process of claim 11 wherein the olefin is propylene.

15. The process of claim 11 wherein the molar ratio of hydrogen peroxide to olefin in the range of from about 10:1 to about 1:10.

16. A process for producing an epoxide comprising reacting an olefin with hydrogen peroxide in water solvent in the presence of a catalyst comprising a titanium zeolite chemically treated with a modifier selected from the group consisting of palladium, platinum, and copper compounds, wherein the modifier is added as a solution and the catalyst is not recovered prior to use in olefin epoxidation.

17. The process of claim 16 wherein the zeolite is titanium silicalite.

18. The process of claim 16 wherein the catalyst is comprised of from 0.01 to 2 weight percent of the modifier metal.

19. The process of claim 16 wherein the olefin is propylene.

20. The process of claim 16 wherein the molar ratio of hydrogen peroxide to olefin in the range of from about 10:1 to about 1:10.

* * * * *